United States Patent [19]

Dunks et al.

[11] Patent Number: 5,089,180
[45] Date of Patent: Feb. 18, 1992

[54] METHOD OF PREPARING COMPOSITE SINGLE-PIECE INTRAOCULAR LENSES WITH COLORED HAPTICS

[75] Inventors: Gary B. Dunks, Upland; Akira Yamada, Claremont, both of Calif.; Oh-Seung Kwon, Woodburg, Minn.; Andrea Borgelt, Riverside, Calif.

[73] Assignee: Iolab Corporation, Claremont, Calif.

[21] Appl. No.: 401,368

[22] Filed: Aug. 31, 1989

[51] Int. Cl.⁵ .............................................. B29D 11/00
[52] U.S. Cl. ...................................... 264/1.7; 264/2.7; 623/6
[58] Field of Search ................. 264/1.7, 1.8, 1.9, 2.7; 351/162; 623/901, 6

[56] References Cited

U.S. PATENT DOCUMENTS

| | | | |
|---|---|---|---|
| 3,454,332 | 7/1969 | Siegel | 264/1.7 |
| 3,619,044 | 9/1971 | Kamath | 351/160 |
| 4,093,361 | 6/1978 | Erickson et al. | 351/160 |
| 4,102,567 | 7/1978 | Cuffe et al. | 351/160 |
| 4,121,885 | 10/1978 | Erickson et al. | 264/1.7 |
| 4,460,523 | 7/1984 | Nufe | 264/1.7 |
| 4,528,311 | 7/1985 | Beard et al. | 524/91 |
| 4,558,931 | 12/1985 | Fuhrman | 351/160 |
| 4,636,212 | 1/1987 | Posin et al. | 351/162 |
| 4,638,025 | 1/1987 | Fuhrman | 351/162 |
| 4,676,791 | 6/1987 | LeMaster et al. | 623/6 |
| 4,687,485 | 8/1987 | Lim et al. | 623/6 |
| 4,716,234 | 12/1987 | Dunks et al. | 548/259 |
| 4,774,036 | 9/1988 | LeMaster et al. | 264/1.7 |
| 4,803,254 | 2/1989 | Dunks et al. | 525/477 |
| 4,813,956 | 3/1989 | Gupta | 623/6 |
| 4,961,746 | 10/1990 | Lim et al. | 264/1.7 |

FOREIGN PATENT DOCUMENTS

| | | |
|---|---|---|
| 0331457 | 9/1989 | European Pat. Off. |
| 2181355A | 4/1987 | United Kingdom |

OTHER PUBLICATIONS

Choyce, D. P., "The Latest Facts and Figures on Anterior Chamber Lens Implants," *Proc. Roy. Soc. Med.*, vol. 69, pp. 906-908 (Dec. 1976).

*Primary Examiner*—James Lowe

[57] ABSTRACT

Composite acrylic polymer rods having clear central regions and colored peripheral regions are prepared by polymerizing a flowable solution comprising acrylic monomer, dye and, dissolved therein, acrylic polymer, around a rod of acrylic polymer. Alternatively, a rod of acrylic polymer surrounded by a flowable mixture comprising partially polymerized acrylic monomer and dye is subjected to polymerization conditions to polymerize the flowable mixture.

15 Claims, No Drawings

METHOD OF PREPARING COMPOSITE SINGLE-PIECE INTRAOCULAR LENSES WITH COLORED HAPTICS

BACKGROUND OF THE INVENTION

The present invention relates to a method for forming a composite rod of acrylic resin, said rod comprising a colorless or clear central portion and a peripheral surrounding portion of a darker color. The composite rods made according to this invention can be used to form single-piece intraocular lenses (IOL's) having a central lens body and colored positioning loops.

Single-piece IOLs, commonly fabricated of the polymer polymethylmethacrylate (PMMA), are widely used for implantation in both anterior and posterior chambers of the eye. The IOLs commonly comprise a central lens body having positioning loops extending radially therefrom. It having been recognized that IOLs which are fabricated entirely of clear, colorless material can be difficult to visualize and manipulate during implantation, there have been suggestions to form the positioning loops of a colored material. Numerous IOLs having separate, colored positioning loops have been marketed. Methods for fabricating single-piece IOLs having colored positioning loops have also been suggested.

U.S. Pat. No. 4,813,956, issued to Gupta on Mar.21, 1989, discloses a method of forming single-piece intraocular lenses comprising the steps of forming a thin sheet of colored polymethyl methacrylate, coring the sheet to form holes therein, filling the holes with a clear or differently colored PMMA material, polymerizing the colored and clear or differently colored PMMA material comprising the sheet and filled holes, cutting core members from the polymerized sheet each having an inner circular region of PMMA material and an outer region of colored PMMA material and machining a single-piece intraocular lens from a core member to have a central lens body of PMMA material and colored PMMA positioning loops extending from and integral with the central lens body.

U.S. Pat. Nos. 4,676,791 and 4,774,036, issued to LeMaster et al. on June 30, 1987, and Sept. 27, 1988, respectively, disclose IOLs with color ringed or rimmed edges. The lenses can be fabricated by passing a clear rod of optical quality PMMA through an extrusion orifice and coating the circumference of the rod with a layer of colored PMMA or other compatible material. Other methods of fabrication can include the introduction of a suitable dye into the outer regions of the rod, or joining the clear central region to a ring of colored material by thermal or adhesive bonding or other known processes. By lathing loops from the colored portion of the rod and lathing the optic from the clear portion of the rod, there is manufactured a single piece lens with colored loops and partially colored optic.

U.S. Pat. No. 4,687,485, issued to Lim et al. on Aug. 18, 1987, discloses an intraocular lens having colored positioning legs. The patent suggests that such lenses may be made by forming a rod of an appropriate polymer, such as polymethylmethacrylate, centering the rod in a tube, pouring into the tube a solution of initiator, monomer and dye, and allowing the solution to polymerize. The resultant two-layered rod can be cut into discs which can be lathe cut and machined to form an IOL.

U.S. Pat. No. 3,619,004, issued to Kamath on Nov. 9, 1971, discloses contact lenses having an edge of a plastic material which is softer than the poly (4-methyl pentene-1) from which the remainder of the lens is formed. The patent suggests that the lens may be prepared by forming a rod of poly (4-methyl pentene-1), submerging the rod in a vessel containing an aqueous solution of acrylic acid and a homopolymerization inhibitor, subjecting the submerged rod to gamma radiation to yield a rod grafted with a swollen polyacrylic acid polymer cladding. Buttons may be cut from the composite rod, and lenses machined from the buttons.

The methods heretofore taught for preparing composite rods from which IOLs with colored positioning loops may be machined have not been entirely satisfactory. Acrylic polymers such as PMMA, the material of choice for IOLs, swell in the presence of acrylic monomers. Thus, when one surrounds a PMMA rod with a mixture of MMA monomer, initiator, and dye (with the intention of then polymerizing the MMA/dye to form a colored peripheral portion), the PMMA rod can swell up to about two and one half times its normal size. In so doing, of course, the MMA and dye penetrate the PMMA rod so that it is not possible to obtain a final composite rod having two distinct regions, a clear central region and a peripheral region of a different color.

SUMMARY OF THE INVENTION

Novel methods for preparing composite acrylic polymer rods having clear central regions and colored peripheral regions have now been found. According to one method of this invention, an intermediate product is formed by surrounding a rod of acrylic polymer from which a clear, transparent, refractive lens body can be fashioned, with a flowable solution comprising dye, acrylic monomer and acrylic polymer substantially dissolved therein. The intermediate product is then subjected to conditions under which the solution will polymerize to an acrylic polymer to yield a composite acrylic polymer rod.

In a second related method of this invention, an intermediate product is formed by surrounding a rod of acrylic polymer with a flowable pre-polymer mixture comprising partially polymerized acrylic monomer and a dye. The intermediate product is then subjected to conditions under which polymerization of the partially polymerized acrylic monomer is completed to yield the desired composite rod having two distinct regions.

Using either of these methods, composite rods having two distinct regions, a clear central portion and a peripheral portion of a different color, may be obtained. These composite rods can be used to form single-piece intraocular lenses (IOL's) having a central lens body and colored positioning loops.

DETAILED DESCRIPTION OF THE INVENTION

The composite rods of this invention are comprised of acrylic polymers. The term "acrylic polymer" includes the preferred polyalkylacrylates, such as polymethylmethacrylate, as well as copolymers of two or more acrylic monomers such as methylmethacrylate and butylmethacrylate.

In addition, the term "acrylic polymer" encompasses copolymers of acrylic monomer with other suitable monomers. In particular, copolymers of acrylic monomers with ultraviolet absorbing monomers, as are known in the art, are included. Examples of such UV-absorbing monomers are the 2-hydroxy-5-acryloxyphenyl-2H-benzotriazoles disclosed in U.S. Pat. No. 4,528,311, the 2-(2'-hydroxy-5'-acryloyloxyalkoxyphenyl)-2H-benzotriazoles disclosed in U.S. Pat. No. 4,716,234, and the vinylsilylalkoxy arylbenzotriazols disclosed in U.S. Pat. No. 4,803,254. The disclosures of these three patents are hereby incorporated by reference. A particularly preferred UV absorbing monomer is the compound 2-(2'-hydroxy-5'-methacrylyloxypropyl-3'-tert-butylphenyl)- 5-chloro-2H-benzotriazole. UV absorbers such as these are generally incorporated into the acrylic polymer from which the optic portion of an IOL is made in the amount of about 0.1 to 10, preferably 1 to 5, and most preferably about 3 weight % of the polymer.

For best results, the monomer(s) from which the acrylic polymer is to be made are contacted with a catalytic quantity of a polymerization initiator. Suitable initiators are known in the art and include, for example, bis [4-t-butyl cyclohexyl]peroxydicarbonate, azobisisobutyronitrile (AIBN), and difunctional peroxyesters such as mixtures of t-amyl peroxyneodeconoate and 2,5-dimethyl-2,5-bis(2-ethyl hexoyl peroxy)hexane. Generally, the initiators are used in the amount of about 0.01 to 1.00 weight % of total monomers.

The dyes which may be used in the colored peripheral portion of the composite rods should be soluble in the selected monomer(s). Examples of suitable dyes for use with acrylic monomers such as MMA include D&C violet #2 and D&C green #6. The amount of dye utilized is not critical, the upper limit generally being defined by the solubility of the dye. Excellent results have been obtained using D&C violet #2 in the amount of about 0.14 to 0.18 weight % of the monomer mixture in which it is dissolved.

The reaction mixture of monomer(s), initiator and optionally dye are heated to induce polymerization. The temperature to which the mixture must be heated, and the time of heating, will vary depending on the monomers and initiator selected. Generally speaking, however, polymerization can usually be completed by heating to a temperature between about 40° and 60° C. over a period of about 20 to 120 hours.

In one method of the invention, a rod of acrylic polymer (preferably comprising a copolymer of at least one acrylic monomer and at least one UV absorbing monomer) from which a clear, transparent, refractive lens body can be fashioned is surrounded with a solution comprising acrylic polymer substantially dissolved in a mixture comprising acrylic monomer and dye. The amount of acrylic polymer substantially dissolved in the solution should be such that the solution remains flowable but also should be a quantity effective to inhibit swelling of an acrylic polymer placed in contact with that mixture. The solution desirably has a viscosity between about 1500 and 10,000 cps (Brookfield viscometer). Generally, the amount of acrylic polymer dissolved in the mixture is about 5 to 25 weight % of the solution.

The dyes which may be used in the colored peripheral portion of the composite rods should be soluble in the selected monomer(s). Examples of suitable dyes for use with acrylic monomers such as MMA include D&C violet #2 and D&C green #6. The amount of dye utilized is not critical, the upper limit generally being defined by the solubility of the dye. Excellent results have been obtained using D&C violet #2 in the amount of about 0.14 to 0.18 weight % of the monomer mixture in which it is dissolved.

A preferred method for preparing the solution involves subjecting to polymerization conditions a mixture of a desired acrylic monomer or monomers initiator and, optionally, dye. The resulting hard polymeric material may be ground to a suitable particle size and can then be dissolved in a mixture of desired acrylic monomer or monomers initiator and, optionally, dye, to form the flowable, colored solution. One can incorporate the dye in the PMMA particles, in the monomer mixture in which those particles are dissolved, or both.

In a second method of this invention, a rod of acrylic polymer is surrounded with a flowable pre-polymer mixture comprising partially polymerized acrylic monomer and a dye. The partially polymerized mixture of monomer(s) and dye may be prepared by heating the monomers and dye, preferably in the presence of a catalytic quantity of initiator, for a period of time sufficient to partially polymerize the monomers but still retain a flowable reaction mixture. The temperature to which the mixture is heated to induce polymerization will depend upon the duration of heating, and vice versa, but, generally speaking, a suitable partially polymerized mixture may be obtained by heating the monomer(s), dye and initiator for a period of about 0.1 to 3 hours at a temperature of about 40° to 100° C. The resulting pre-polymer mixture should preferably have a viscosity in the range of about 1500 to 10000 cps. After an optical rod is surrounded with this partially polymerized monomer/dye mixture, the resulting product is subjected to conditions to complete the polymerization of the partially polymerized monomer. The conditions required to complete polymerization will depend on the extent to which the monomer has already been polymerized, it being kept in mind that total polymerization of the acrylic monomer(s) will generally occur upon exposure to temperatures between about 40° and 60° C. for a period of about 20 to 120 hours.

The composite rods made according to this invention can be used to prepare IOLs. By lathing loops from the colored portion of the rod and lathing the optic from the clear portion of the rod, there is manufactured a single piece lens with colored loops and clear optic.

The methods of this invention are further illustrated by the following examples, intended to be illustrative only and not limiting of scope.

EXAMPLE 1 a. Optic Rod Synthesis

Methyl methacrylate (MMA, 15,000 g) was passed through a column of basic resin (DH-4, Scientific Polymer Products, 0.02 g resin per g of MMA) over 15 hours to reduce the inhibitor (4-methoxyphenol, MEHQ) concentration to less than 1 ppm. The uninhibited MMA (14,544 g) was charged to a 22 L, 3-neck flask fitted with mechanical stirring and a nitrogen inlet. Under a slow nitrogen purge and with slow stirring, 450.4 g UV-absorbing monomer 2-(2'-hydroxy-5'-methacrylyloxypropyl-3'-tert-butylphenyl)-5-chloro-2H-benzotriazole (hereinafter referred to as "X-monomer") was added followed by 7.2968 g bis [4-t-butyl cyclohexyl]peroxydicarbonate initiator (PERKADOX® 16N, available from Noury Chemicals). The mixture was stirred at ambient temperature for 15 minutes to effect solution and was then filtered using a Rainin 311500, 350 mL filter (equipped with Whatman #3 paper) into a 22 L receiver with a self-contained water aspirator pump (Cole-Parmer, J-7049-00). The filtrate was filtered again through 0.2 μm Nylon-66 membrane (Rainin, 38-111) into a 22 L receiver, using the water aspirator. The polished solution was sparged with nitrogen for 15 seconds using a course frit Pyrex filter stick. A nitrogen blanket was maintained over the solution.

Nylon tubing (Nylon-6, 1.13 cm diameter, 0.066 mm wall thickness) was cut to approximately 1 m lengths and thermally sealed at one end. Each sealed tube was expanded using nitrogen (9.5 psig) and the seal tested for leaks in water. A tube was charged with MMA/X monomer solution (approximately 100 g.) using a metering pump (Cole Parmer model J-7616 with J-7002 head) to provide a finished rod about 91 cm long. The filled tube was then attached to a nitrogen source (2.5 psig) and thermally sealed under pressure. The completely sealed tube was suspended at ambient temperature in the oven. This process was repeated until the MMA/X monomer solution was consumed.

The sealed tubes were placed in an oven programmed to provide the following polymerization and curing cycles: Heating from ambient temperature to 42° C. over 0.5 hours; maintaining at 42° C. for 58 hours; ramping to 110° C. over 1 hour; maintaining at 110° C. for 4 hours; cooling to 30° C. over 2.5 hours. The nylon tubing was stripped from the resulting polymer rods which were then machined to provide optic zones.

b. Violet-PMMA (Pre-Polymer Mixture)

A 6L Erlenmeyer flask fitted with magnetic stirring was charged with MMA (4591 g), D&C violet #2 dye (6.9231 g) and PERKADOX ™ 16N initiator (2.3019 g). The mixture was stirred at ambient temperature for 30 minutes and then filtered through Whatman #3 paper (water aspirator). The filtered solution was charged to screw-cap test tubes (2.5×20 cm). The test tubes, in racks, were placed in an oven and subjected to the following polymerization and curing cycle: heating at 65° C. for 18 hours; ramping to 80° C. over 0.5 hour; maintaining at 80° C. for 5 hours; ramping to 110° C. over 0.5 hour; maintaining at 110° C. for 4 hours; cooling to 30° C. over 2.5 hours. Subsequent to polymerization, the test tubes were broken and the polymer rods removed. The rods were washed thrice with deionized water and dried in vacuo at 70° C.

The violet-PMMA rods were passed through a grinder (Cumberland, 284A) fitted with a screen containing 2.4 mm openings.

The granules produced were sieved using #12 (1.70 mm) and #20 (0.85 mm) screens and the $-12+20$ fraction was used in subsequent operations (approximately 80% of the granules).

A special 22 L flask fitted with heavy-duty mechanical stirring, nitrogen inlet and a bottom outlet was charged with MMA (10448 g), D&C violet #2 dye (15.6930 g), PERKADOX ™ 16N initiator (6.5493 g) and violet-PMMA granules as prepared above (2613.8 g). The pre-polymer mixture was stirred under nitrogen at ambient temperature for 60±5 minutes.

c. Composite Rods

Both ends of a Pyrex tube (2.5 cm i.d.×15 cm long) were wrapped with Teflon polytetrafluoroethylene tape, then one end was fitted with a Teflon cap equipped with an optic rod as prepared in section (a). Violet prepolymer mixture from (b) above was charged to the tube (approximately 64 g) from the bottom outlet of the flask. A second cap was secured to the mold which is thus sealed and the rod was placed in an oven maintained at 65° C. The mold was then subjected to the following polymerization and curing cycle: 18 hours at 65° C.; ramping to 80° C. over 0.5 hour; maintaining at 80° C. for 5 hours; ramping to 110° C. over 0.5 hour; maintaining at 110° C. for 4 hours; cooling to 30° C. over 2.5 hours. The composite rods were then forced out of the Pyrex molds and possessed a clear, central optic region and a peripheral, violet region.

EXAMPLE 2 a. Violet PMMA (Prepolymer Mixture)

A mix vessel was charged with methyl methacrylate (MMA), (5190±10 g) and stirring was initiated. D&C violet #2 dye (7.8±0.3 g) and mixed initiator (2.6 g t-amyl peroxyneodecanoate (Lupersol 546-M75, Pennwalt Chemicals)±0.3 g 2,5-dimethyl-2,5-bis(2-ethyl hexoyl peroxy)hexane (USP-245, Witco Chemical)) was added. The addition port was closed and stirring at ambient temperature was continued for 15 minutes. Without interrupting the stirring, the addition port was loosened to allow pressure relief and screw-cap test tubes (2.5×20 cm) were filled (approximately 54 grams each) through the vessel dump valve. The test tubes in racks were placed in an oven and subjected to the following polymerization and curing cycle: 60° C. for 0.5 hours; ramping down to 45° C. over 0.25 hours; maintaining at 45° C. for 17.0 hours; ramping to 110° C. over 5.0 hours; maintaining at 110° C. for 4.0 hours; cooling to 30° C. over 2.0 hours. Subsequent to polymerization, the test tubes were broken and the polymer rods removed. The rods were washed twice with tap water, then once with distilled water and dried in a vacuum oven at 65°±5° C. for 3 to 8 hours.

The violet-PMMA rods were passed through a grinder (Cumberland, 284A) fitted with a screen containing 2.4 mm openings. The granules produced were sieved using #12 (1.70 mm) and #20 (0.85 mm) screens. The course granules (+12) were reground and sieving continued until all material passed the #12 screen. The $-12+20$ fraction was used in subsequent operations (approximately 80% of the granules).

A mix vessel was charged with MMA (11700±25 g) and stirring initiated. D&C violet #2 dye (18.2±0.6 g), mixed initiator (18.2 g t-amyl peroxyneodecanoate±0.6 g 2,5-dimethyl-2,5-bis(2-ethyl hexoyl peroxyl)hexane, approximately 9.8 mL) and violet PMMA granules (1303±25 g) were added. The addition port was closed and stirring continued at ambient temperature until the viscosity at 6 rpm was 2500-7500 cps (Brookfield viscosity) (24 to 72 hours).

b. Composite Rods

One end of a Pyrex tube (2.8 o.d.×2.5 i.d.×15 cm long) was wrapped with 44±1 Teflon polytetrafluoroethylene tape and a Teflon polytetrafluoroethylene cap was fitted to the tube. The opposite end of the tube was wrapped with 18±1 cm Teflon polytetrafluoroethylene tape. A lecithin/hexane solution was prepared by pouring lecithin (24±1 g) into a brown glass, screw-top 1 L bottle, then adding hexane (800±1 g) and agitating the resulting mixture to thoroughly dissolve the lecithin. The molds were filled with the lecithin/hexane solution then inverted to pour the solution out. The molds were allowed to stand in the inverted position for a minimum of 3 hours to dry. After drying, clear optic rods (prepared, e.g., as in Example 1, part a) were carefully installed in the center of each mold, without contact of the optic rod with the lecithin coated mold surface. The molds were then filled with violet-PMMA syrup (prepolymer mixture of part (a)) and topped with Teflon polytetrafluoroethylene caps. The filled molds were placed in an oven at ambient temperature and then subjected to the same polymerization/curing cycle set forth above in part (a) of this Example. The cured rods were forced out of the molds and stored. They possessed two clearly distinct regions, a clear, central optic region and a violet peripheral region.

EXAMPLE 3

An Erlenmeyer flask was charged with 100 parts MMA (inhibited with 10 ppm of MEHQ), 0.15 parts violet dye (D&C Violet #2), 0.04 parts of t-amyl peroxyneodecanoate and 0.01 parts 2,5-dimethyl-2,5-bis(2-ethyl hexoyl peroxy)hexane. The mixture was stirred until a homogenous solution was obtained and then the mixture was poured into molds (as used, e.g., in Example 1(c)). The molds were placed in a pre-heated oven (60° C.) for 90 minutes. Then the molds were taken out of the oven and 8.5 mm optic rods were inserted therein. The polymerization was continued in a programmed oven as follows: 45° C. for 17 hours; ramp to 110° C. for 5 hours; 110° C. for 4 hours; cooling to 30° C. for 2 hours. The resulting rods had 7.1 mm dye-free zones and 1% MMA residue.

EXAMPLE 4

A vessel was charged with MMA (250 g) and stirring was initiated. D&C violet #2 dye (0.375 g) and PERKADOX TM 16N (0.125 g) were added. The solution was stirred under gentle heating (approximately 40° C.) and was then charged in screw-cap test tubes (2.5×20 cm). The test tubes were placed in an oven maintained at 100° C. and subjected to that temperature for one hour.

Upon removing the test tubes from the oven, the viscous prepolymer contained therein was charged into two prepared glass molds (e.g., as used in Example 1(a)) fitted with optic rods (9.5 mm, prepared, for example, as in Example 1(a)). The molds were secured in fixtures and subjected to a polymerization/curing cycle as follows: 100° C. for 2 hours; ramp to 80° C. over 1.5 hours; maintain at 80° C. for 15 hours; ramp to 100° C. over 0.7 hours; maintain at 100° C. for 2 hours; ramp to 130° C. over 1.5 hour; maintain at 130° C. for 3 hours; cool to 25° C. over 1.0 hour. The resulting rods had a central dye free zone of average diameter 7.51±0.11 mm.

EXAMPLE 5

A vessel was charged with MMA (50 g) and stirring was initiated. D&C violet #2 dye (0.075 g) and AIBN (0.025g) were added. The violet solution was stirred under gentle heating (approximately 40° C.). The solution was then charged into screw cap test tubes (2.5×20 cm) and placed in a constant temperature water bath set at 65° C. The water bath was maintained at 65° C. for 3.5 hours.

Upon removing the test tubes from the water bath, the viscous solution was charged into a prepared mold (e.g., as in Example 1(a)) fitted with an optic rod (11.0 mm, prepared, for example as in Example 1(a)). The mold was secured in a holding fixture and placed in a water bath at 55° C., where it was maintained for 17 hours. The mold was then placed in an oven at 80° C. for two hours, at 100° C. for two hours, and at 130° C. for three hours, before cooling to room temperature. The resulting composite rod had a central dye-free zone of average diameter 9.76±0.10 mm.

What is claimed is:

1. A method of preparing an intraocular lens having a central lens body and positioning loops extending radially therefrom, said positioning loops being of a different color than said central lens body, comprising the steps of:
   (a) surrounding a rod of a first clear acrylic polymer with a flowable solution having a viscosity between about 1500 and 10,000 cps comprising acrylic monomer, dye and a second acrylic polymer substantially dissolved therein,
   (b) subjecting the product of step (a) to conditions to induce polymerization of said acrylic monomer so as to form a composite rod having a clear central region and a dyed peripheral region, and
   (c) lathing said lens from said composite rod so that said loops are lathed from said dyed peripheral region of said composite rod and said central lens body is lathed from said central region of said composite rod.

2. The method of claim 1 wherein said first acrylic polymer comprises a copolymer of methylmethacrylate and at least one UV-absorbing monomer.

3. The method of claim 2 wherein said UV-absorbing monomer is 2-(2'-hydroxy-5'-methacrylyloxypropyl-3'-tert-butylphenyl)-5-chloro-2H-benzotriazole.

4. The method of claim 1 wherein said second acrylic polymer is polymethylmethacrylate and said acrylic monomer is methylmethacrylate.

5. The method of claim 1 wherein said dye is selected from the group consisting of D&C violet #2 and D&C green #6.

6. The method of claim 1 wherein said pre-polymer mixture comprises about 0.14 to 0.18 weight % dye.

7. The method of claim 1 wherein said pre-polymer mixture further comprises a catalytic quantity of a polymerization initiator.

8. The method of claim 1 wherein said pre-polymer mixture comprises about 5 to 25 weight % of said dissolved acrylic polymer.

9. A method of preparing an intraocular lens having a central lens body and positioning loops extending radially therefrom, said positioning loops being of a different color than said central lens body, comprising the steps of:
   (a) surrounding a rod of a clear acrylic polymer with a flowable mixture having a viscosity between about 1500 and 10,000 cps comprising partially polymerized acrylic monomer and dye.
   (b) subjecting the product of step (a) to conditions to induce polymerization of said acrylic monomer so as to form a composite rod having a clear central region and a dyed peripheral region, and
   (c) lathing said lens from said composite rod so that said loops are lathed from said dyed peripheral region of said composite rod and said central lens body is lathed from said central region of said composite rod.

10. The method of claim 9 wherein said clear acrylic polymer comprises a copolymer of methylmethacrylate and at least one UV-absorbing monomer.

11. The method of claim 10 wherein said UV-absorbing monomer is 2-(2'-hydroxy-5'-methacrylyloxypropyl-3'-tert-butylphenyl)-5-chloro-2H-benzotriazole.

12. The method of claim 9 wherein said acrylic monomer is methylmethacrylate.

13. The method of claim 9 wherein said dye is selected from the group consisting of D&C violet #2 and D&C green #6.

14. The method of claim 9 wherein said flowable mixture comprises about 0.14 to 0.18 weight % dye.

15. The method of claim 9 wherein said flowable mixture further comprises a catalytic quantity of a polymerization initiator.

* * * * *